(12) United States Patent
Escriba-Ruiz

(10) Patent No.: US 8,778,995 B2
(45) Date of Patent: Jul. 15, 2014

(54) USE OF HYDROXYOLEIC ACID AND RELATED COMPOUNDS IN THE MANUFACTURE OF DRUGS

(75) Inventor: Pablo Vicente Escriba-Ruiz, Palma de Mallorca (ES)

(73) Assignee: Universitat de les Illies Balears, Palma de Mallorca (ES)

( * ) Notice: Subject to any disclaimer, the term of this patent is extended or adjusted under 35 U.S.C. 154(b) by 763 days.

(21) Appl. No.: 12/939,641

(22) Filed: Nov. 4, 2010

(65) Prior Publication Data

US 2011/0136906 A1    Jun. 9, 2011

Related U.S. Application Data

(62) Division of application No. 12/082,938, filed on Apr. 15, 2008, now Pat. No. 7,851,507, which is a division of application No. 10/488,726, filed as application No. PCT/ES02/00475 on Oct. 9, 2002, now abandoned.

(30) Foreign Application Priority Data

Oct. 11, 2001 (ES) .................................. 200102269

(51) Int. Cl.
*A61K 31/201* (2006.01)
(52) U.S. Cl.
CPC .................................... *A61K 31/201* (2013.01)
USPC .......................................................... 514/558
(58) Field of Classification Search
None
See application file for complete search history.

(56) References Cited

U.S. PATENT DOCUMENTS

| 4,601,856 A | 7/1986 | Suzuki et al. |
| 5,798,348 A * | 8/1998 | Alemany ...................... 514/182 |
| 6,096,784 A | 8/2000 | Lerner et al. |
| 6,214,875 B1 | 4/2001 | Yang |
| 2003/0130346 A1 * | 7/2003 | Kuzela et al. ................. 514/547 |

FOREIGN PATENT DOCUMENTS

| WO | 87/04926 | 8/1987 |
| WO | 94/01100 | 1/1994 |
| WO | 96/31457 | 10/1996 |
| WO | 02/051406 | 7/2002 |

OTHER PUBLICATIONS

Sebastiano, B., et al. "Vaccenic acid feeding increases tissue levels of conjugated linoleic acid and suppresses development of premalignant lesions in rat mammary gland." *Nutrition and Cancer*(2001) vol. 41 (1-2) pp. 91-97.
Awad, A. B., et al. "18:1 n7 fatty acids inhibit growth and decrease inositol phosphate release in HT-29 cells compared to n9 fatty acids." *Cancer Letters*(1995) vol. 91 (1) pp. 55-61.
Sausville et al. Cancer Research, 2006, vol. 66, pp. 3351-3354.
Johnson et al. British J. of Cancer, 2001, 84(10):1424-1431.
Martinez et al. The Journal of Pharmacology and Experimental Therapeutics, 2005, vol. 315, No. 1, pp. 466-474.
Martinez et al. Molecular Pharmacology, 2005, vol. 67, No. 2, pp. 531-540.

* cited by examiner

*Primary Examiner* — James D Anderson
(74) *Attorney, Agent, or Firm* — Ladas & Parry LLP

(57) ABSTRACT

Use of hydroxyoleic acid and its analogous compounds in the manufacture of drugs. Describes the use of hydroxyoleic acid and its analogs of general formula I: $COOH-CHR-(CH_2)_m-CH=CH-(CH_2)_n-CH_3$, in which m and n have, independently, a value of 0-15 and R can be any residue with molecular weight below 200 Da, in the manufacture of drugs that can be used in the treatment of cancer, hypertension, obesity or diseases mediated by alteration of the membrane structure and the consequent regulation of G-proteins or of the receptors coupled to them.

3 Claims, 10 Drawing Sheets

USE OF HYDROXYOLEIC ACID AND RELATED COMPOUNDS IN THE MANUFACTURE OF DRUGS

CROSS REFERENCE APPLICATIONS

Figure 1:

This application is a divisional of U.S. patent application Ser. No. 12/082,938 filed Apr. 15, 2008 now U.S. Pat. No. 7,851,507, which is a divisional of U.S. patent application Ser. No. 10/488,726 filed Aug. 26, 2004 now abandoned which is a 371 of PCT/ES2002/000475 filed Oct. 9, 2002 which claimed priority to Spanish Patent Application No. P200102269 filed Oct. 11, 2001, the contents of which are incorporated herein by reference.

FIELD OF THE INVENTION

The present invention relates to the use of hydroxyoleic (2-hydroxyoleic) acid and molecules of a similar structure as antitumor agents, as agents with hypotensive activity and as agents for inducing reductions in body weight.

The present invention also relates to the use of 2-hydroxyoleic acid and similar compounds for controlling membrane structure, controlling the activity and/or localization of G-proteins and controlling the activity of receptors bound to G-proteins through regulation of membrane structure.

The present invention also relates to the use of 2-hydroxyoleic acid and similar compounds for the manufacture of drugs intended for cancer treatment, of drugs for treating cardiovascular diseases and of drugs for treating problems of body weight and obesity.

BACKGROUND TO THE INVENTION

Fatty acids are molecules of wide application, both in foodstuffs and in industry. 2-Hydroxyoleic acid, the synthesis of which has been described previously (Adam et al., 1998, Eur. J. Org. Chem. 9, 2013-2018), has been used industrially as an emulsifier for preparations of cosmetics.

For example, on the one hand, patent JP 10182338 relates to an oil-in-water emulsifying composition that exhibits low irritability and high compatibility with salts, which contains: [A] nonionic surfactants such as polyoxyethylene sorbitol monolaurate, polyoxyethylene sorbitol monooleate and polyoxyethylene sorbitol monostearate, [B] 2-hydroxy C10-C22 fatty acids such as 2-hydroxystearic acid, [C] oils and [D] water, in which the A/B ratio is between 1:0.01 and 1:2.

Patent JP 09110635 also relates to compositions that can be used as pharmaceutical products, cosmetics and foodstuffs and contain: [A] esters of polyglyceryl fatty acid, [B] 2-hydroxy C10-C22 fatty acids, [C] oils and [D] water, where the weight ratio of A/C and B/C is 2.0 and 0.5 respectively, and have average particle sizes between 10 and 300 nm. These compositions show good stability even in acid conditions or at low viscosity or in the presence of elevated quantities of salts, and therefore are compatible with the skin.

On the other hand, this fatty acid has also been employed as an inhibitor of oleamide hydrolase, an action that is associated with the sleep inducing effect of this substance (U.S. Pat. No. 6,096,784 and WO 9749667).

For example, U.S. Pat. No. 6,096,784 relates to the design and synthesis of oleamide hydrolase inhibitors, responsible for the hydrolysis of a sleep-inducing lipid (cis-9-octadecenamide). The most potent inhibitors possess an electrophilic carbonyl group capable of forming, reversibly, a (thio)hemiacetal or a (thio)hemiacetal for imitating the transition state of a reaction catalyzed by a protease of the cisteine or serine type. In addition to the inhibitory activity, some of the inhibitors displayed agonistic activity that induces sleep in laboratory animals.

The Hexagonal Membrane Structures.

The membrane lipids are able to arrange themselves in a greater number of secondary structures than the proteins and nucleic acids. The typical lipid bilayer of biological membranes is just one of these secondary configurations. Little is known about the abundance and roles of other secondary structures in living cells. One function of these structures was described in a previous work of the inventors: to increase the binding affinity of G-proteins to membranes (Escribá P V, Ozaita A, Ribas C, Miralles A, Fodor E, Farkas and García-Sevilla J A; 1997 Proceedings of the National Academy of Sciences of the USA 94, 11375-11380).

The concept of membrane structure goes far beyond that described in some of the patents of the state of the art (WO 87/04926 and WO 80/11286), in which only membrane fluidity is mentioned, and the concept is extended to a much wider field: the membrane structure. The molecules covered by our patent act on the transition or passage from lamellar to hexagonal structure (FIG. 1).

Examining the prior art cited, in the state of the art there are no other applications connected with 2-hydroxyoleic acid or similar compounds that would be of particular interest in the area of cancer treatment, cardiovascular diseases and/or control of body weight.

There are only descriptions of dietary products (GB 2140668, EP 0611568 and WO 02/0042) or extracts from cultures of *M. cryophilus* (WO 89/11286), which consist of complex mixtures of various compounds that include some of those described in the invention, such as fatty acids, in particular oleic and palmioleic acids, for example, and the use of these mixtures in the treatment of arterial hypertension, for the control of obesity or as antitumor agents, but without ascribing to any of the components of the mixture considered in the present invention, a specific role in the said therapeutic effect. Only WO 02/051406 and WO 94/01100 describe the use of certain fatty acids ($C_{14}$-$C_{20}$) in the treatment of prostate cancer, which is not an object of the present invention, exclusively when using the said fatty acids described in the state of the art.

AIM OF THE INVENTION

The present invention has the aim of finding new applications of 2-hydroxyoleic acid and similar compounds that are unconnected with those described in the state of the art.

A first objective of the present invention is to show that 2-hydroxyoleic acid and its analogs possess activity as antitumor agents.

A second objective of the present invention is to show that 2-hydroxyoleic acid and its analogs possess activity as hypotensive agents.

A third objective of the present invention is to show that 2-hydroxyoleic acid and its analogs possess activity as agents that induce a reduction in body weight.

A fourth objective of the present invention is to show that 2-hydroxyoleic acid and its analogs have application as agents for controlling the transition from lamellar to hexagonal structure of cell membranes. This regulation of membrane structure has an influence on the activity of G-proteins, as well as of the molecular entities of their transduction pathway, i.e. of their route of signal propagation. A large number of drugs acts on the receptors bound to G-proteins by direct interaction with molecules of this type or with the mechanisms connected with the cell signals derived from their activity. 2-Hydroxyoleic acid and its analogs, however, act upon the membrane structure.

The applications described below for 2-hydroxyoleic acid and its analogs have not been cited by anyone previously and their use may prove beneficial for the treatment of certain pathologies. In particular, it has been found that 2-hydroxyoleic acid and its analogs display antitumor activity, hypotensive (or antihypertensive) activity and induce reduction of body weight.

In the present invention the new applications of 2-hydroxyoleic acid and its analogs are substantiated by using experimental models, in particular systems of in vitro analysis, cell culture systems and living organisms. All these analysis models show, without doubt, that 2-hydroxyoleic acid and its analogs are molecules that can be used for making drugs for cancer treatment, for treatment of cardiovascular diseases and for treating subjects with problems of body weight and obesity, as well as other diseases or deficiency conditions based on the control of signals associated with G-proteins, mediated by the lamellar to hexagonal transition of the membrane structure.

DESCRIPTION OF THE INVENTION

In the present invention, "2-hydroxyoleic acid" means α-hydroxyoleic acid, octadecenoic acid C18:1 cis Δ9 or cis-2-hydroxy-9-octadecenoic acid. "Analogs" means those fatty acids that have the double bond shifted one or two positions from the central zone and/or that have the double bond shifted from one to five positions from the central zone and/or have from one to six carbon atoms ($CH_2$ groups) more or less on each side of the double bond and/or that have a residue (R) in position 2 different from OH, with a small atomic mass (Mw less than or equal to 200 Da). It does not matter whether the stereoisomer corresponding to the projection of the R group is R or S. In relation to the various molecules tested, it has been observed that those having the general formulas shown below display some similar effects to hydroxyoleic acid and can therefore be categorized as analogs thereof.

General formula I: $COOH-CHR-(CH_2)_m-CH=CH-(CH_2)_n-CH_3$ in which m and n have, independently, a value of 0-15 and R can be H, OH, $NH_2$, $CH_3$, or some other residue with molecular weight below 200 Da.

In the present invention "G-proteins" means proteins that are guanine nucleotide binding proteins, formed from three subunits (one alpha, one beta and one gamma) that transmit signals from receptors bound to G-proteins, to effectors (adenylyl cyclase, guanylyl cyclase, phospholipase C, ion channels, etc.).

In the present invention "membrane structure" means the secondary structure or arrangement of lipids in natural or synthetic membranes (liposomes).

In the present invention "acute effect" means the effect that is produced in a space of time between minutes and some hours after a single administration of a drug.

In the present invention "chronic effect" means the effect that is produced in a space of time between a few days and several weeks of continuous administration of a drug.

In the present invention "pharmaceutically acceptable forms" means any of those used routinely in the sector, including, non-limitatively: esters, especially ethyl esters for their properties as solubilizers of fatty acids, ethers, amides, salts, etc.

One objective of the present invention is the application of 2-hydroxyoleic acid and its analogs in controlling the transition from lamellar to hexagonal structure of the cell membranes. The molecular basis of this phenomenon lies in the interaction of 2-hydroxyoleic acid and its analogs with membranes and in modulation of the membrane composition and/or structure (Tables 1 and 2).

TABLE 1

Effect of binding of 2-hydroxyoleic acid on the temperature of transition from lamellar to hexagonal structure ($H_{II}$).

| DEPE:2OHOA (mol:mol) | $T_H{}^a$ (° C.) |
|---|---|
| 1:0 (pure DEPE) | 63 |
| 40:1 | 54 |
| 20:1 | 48 |
| 10:1 | 41 |

$^a$ $T_H$ indicates the temperature of transition from lamellar to hexagonal structure.

Table 1 shows the values of the temperature of transition from lamellar to hexagonal structures in membranes of dielaidoyl phosphatidylethanolamine (DEPE). The control value (in the absence of 2-hydroxyoleic) is 63° C. The decrease (concentration-dependent) induced by 2-hydroxyoleic acid (2OHOA) shows that this molecule stabilizes the presence of non-lamellar structures. This important modification of the cell membrane has important consequences for molecular and cellular function. All the analogs of 2-hydroxyoleic tested that have therapeutic activity also induce effects on the membrane structure (Table 2).

TABLE 2

Effect of various analogs of hydroxyoleic acid (phospholipid:analog 20:1 mol:mol) on the lamellar-hexagonal transition of the phospholipid dielaidoyl phosphatidylethanolamine (DEPE)

| | $T_H$ (° C.) |
|---|---|
| Control (DEPE only) | 61 |
| Oleic acid | 45 |
| Aminoleic acid | 49 |
| Methyloleic acid | 50 |
| cis-Vaccenic acid | 53 |
| Nervonic acid | 55 |

Modulation of the Lamellar to Non-lamellar Transition Regulates the Activity of G-proteins.

Figure 5:
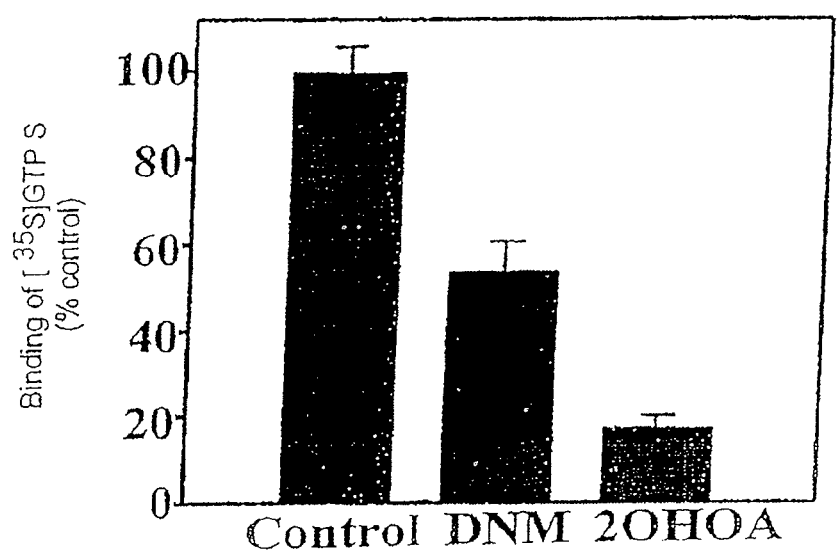

Hydroxyoleic acid and related compounds are capable of modulating the activity of G-proteins, measured by the binding of [$^{35}$S] GTPγS (FIG. 5).

Figure 2:
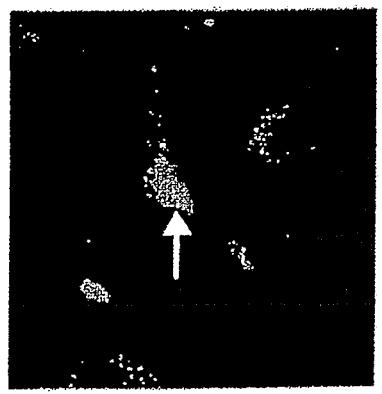
Figure 2:
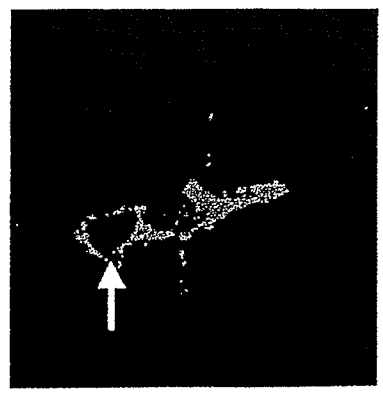
Figure 6:
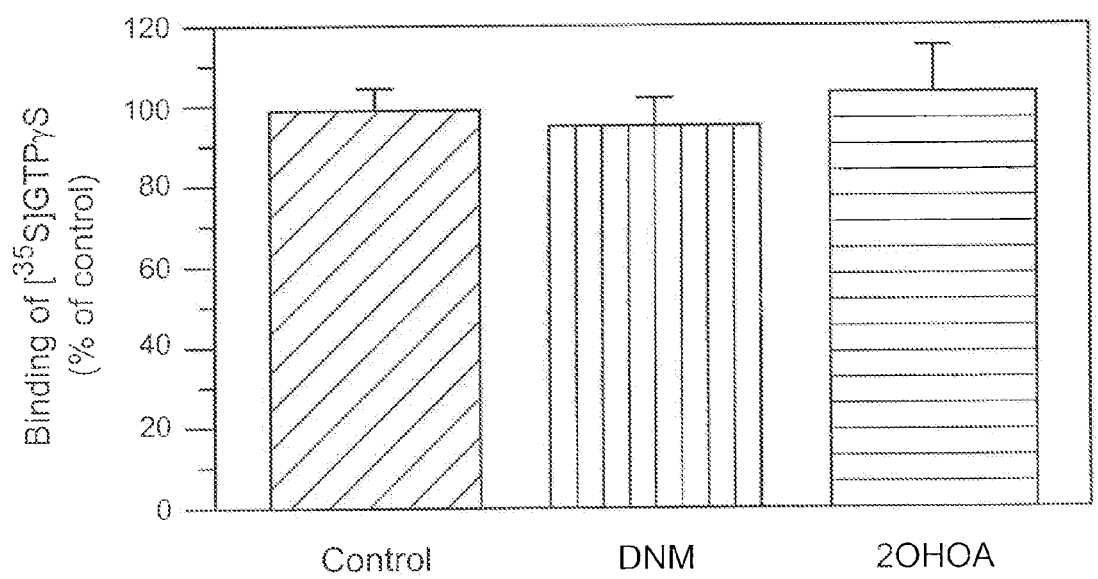

This is because these molecules have an influence on the interaction of G-proteins with membranes and therefore on their cellular localization, as is shown in the photographs from confocal microscopy (FIG. 2). The effect of hydroxyoleic acid and its analogs on the localization and activity of G-proteins is not due to a direct interaction on them. FIG. 6 shows the effect that these molecules have on the activity of purified G-proteins, in the absence of membrane. In contrast to what occurs when the G-proteins are bound to membranes, daunomycin (DNM) and hydroxyoleic (2OHOA), as well as the analogs of the latter, did not have an influence on the activity of these proteins (which are activated only when they are in membranes in contact with receptors bound to G-proteins).

Receptors bound to G-proteins are ubiquitous, making up 80% of the membrane receptors that transmit signals initiated by neurotransmitters, hormones, neuromodulators, cytokines, growth factors, etc. Among other physiological processes, they regulate blood pressure, cell growth and proliferation, and body weight. Accordingly, the molecules described in this invention can regulate the aforementioned physiological processes.

—Tests on Membrane Structure—

The most effective and powerful technique for investigating membrane structure is X-ray diffraction/scattering. Using this technique, we established that the structure of the membrane is altered by 2-hydroxyoleic acid and its analogs. The lowering of the temperature of transition from lamellar to hexagonal structure indicates an important effect on rearrangement of the lipid molecules in the membrane. This regulation of rearrangement forms the basis of the effect exerted by 2-hydroxyoleic acid and its analogs. All the analogs studied, which comply with the general formula, possess activity of membrane modulation and control of cell proliferation (efficacy in cancer), of blood pressure (efficacy in cardiovascular processes) and of body weight (efficacy in obesity).

An objective of the present invention is to demonstrate that 2-hydroxyoleic acid and its analogs possess activity as antitumor agents.

Firstly, the cell cycle is controlled by growth factors which bind to specific receptors on the cell surface. Binding of the said growth factors to the receptors gives rise to a cascade of reactions that are intended to activate mitogenic kinases (cdk) that form dimeric complexes with the proteins associated with the cell cycle called cyclins. The cdk/cyclin complexes regulate the phases of the cell cycle and its progression to produce mitosis and cell division.

Many specific receptors on the cell surface are bound to G-proteins, so that when the growth factor interacts with the receptor the G-protein is activated, triggering the cascade of reactions mentioned earlier.

Accordingly, modulation of the localization and activity of G-proteins will make it possible to control cell growth and cell division.

The mechanism associated with the antitumor effects of 2-hydroxyoleic acid and its analogs is based on the fact that they induce modulation of the localization and activity of G-proteins and other peripheral proteins, such as protein kinase C or the small G-proteins (of the type Ras, Raf, etc.). This modulation is associated with regulation of the structure of the membrane lipids.

It has been found that 2-hydroxyoleic acid acts as an inhibitor of translocation of G-proteins to the nucleus (FIG. 2). In this way, inhibition of cell proliferation is achieved, as was confirmed by the appreciable and significant increases in the levels of the protein p21 and the decreases in the cell cycle proteins cdk2 and cyclins B and D3 (FIGS. 3A and B). Moreover, it has been observed that in cells in culture, 2-hydroxyoleic acid and its analogs induce significant increases in protein kinase C (increase of between 40% and 120%).

Figure 4:
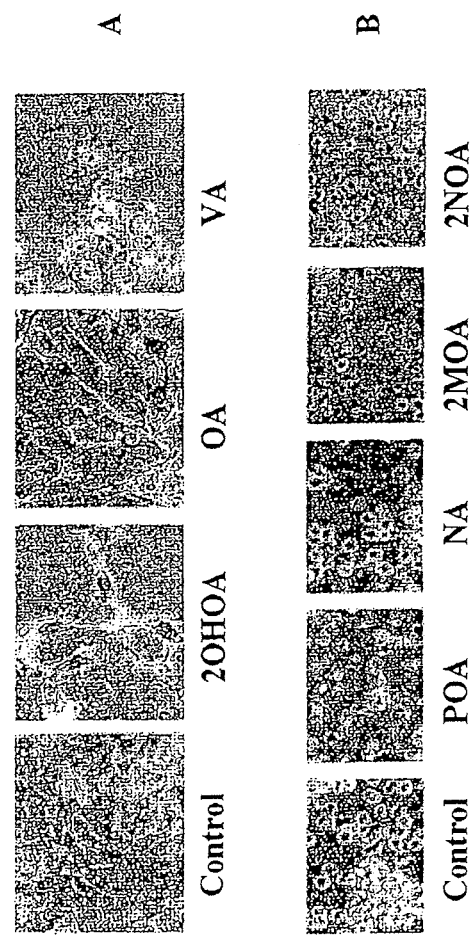

This change in cellular localization of G-proteins produces modulations in their function, greater than those produced by the drug daunomycin, widely used in the treatment of cancer. These changes have important inhibitory effects on the proliferation and survival of tumor cells (FIG. 4).

An important regulator of the cell cycle is the protein p53, which exerts a negative type of control by slowing down cell division at the level of G1 (the stage before mitosis). This protein is synthesized by the cell itself in response to the appearance of alterations of the DNA. If the replicated DNA can have a negative influence on the daughter cells, the p53 protein is activated, giving rise to apoptosis (programmed cell death). Activation of the said protein p53 means that other genes are expressed that code for regulator proteins such as p21, p27, p16, etc., which inhibit the activity/expression of the cyclins and cdks (involved in the process of the cell cycle).

In many types of tumor cells, the p53 protein appears to be mutated and/or inactive, and proliferation of transformed (cancerous) cells occurs. The presence of 2-hydroxyoleic acid and/or its analogs in the cells induces activation of the signal pathway associated with p53, which induces the start of apoptosis or stopping of the cell cycle in various types of tumor cells. With the aim of carrying out the first objective of the present invention, in vitro and in vivo models were used. In this connection, 2-hydroxyoleic acid and all the structural analogs that comply with general formula I described earlier have been shown to possess considerable antitumor capacity. The molecules that are analogs of 2-hydroxyoleic (2-hydroxy-cis-9-octadecenoic) acid tested were: 2-methyl-oleic (2-methyl-cis-9-octadecenoic)acid, 2-amino-oleic (2-amino-cis-9-octadecenoic)acid, oleic (cis-9-octadecenoic)acid, palmitoleic (cis-9-hexadecenoic)acid, cis-vaccenic (cis-11-octadecenoic)acid and nervonic (cis-15-tetracosenoic)acid. These molecules have been shown to halt cell proliferation or induce the death of various types of tumor cells (e.g. human lung cancer cells A549, Jurkat T lymphocytes, etc.) (FIG. 4). These results demonstrate the antitumor activity of the fatty acids described and show that the basic structure of 2-hydroxyoleic acid can have small variations without altering its antitumor activity.

Other molecular models enabled us to confirm that 2-hydroxyoleic acid and its analogs possess antitumor activity that is greater than that presented by other antitumor drugs, for example the anthracyclines, and they are therefore compounds of high therapeutic interest. In membranes of 3T3 fibroblasts, we succeeded in proving that the presence of 200 µM of 2-hydroxyoleic acid and/or oleic acid (one of the analogs of 2-hydroxyoleic acid) induces inhibition of 75-84% in the activity of G-proteins in NIH 3T3 cells, whereas 200 µM of daunomycin induces an inhibition of 46% in the said activity (FIG. 5).

Figure 8:
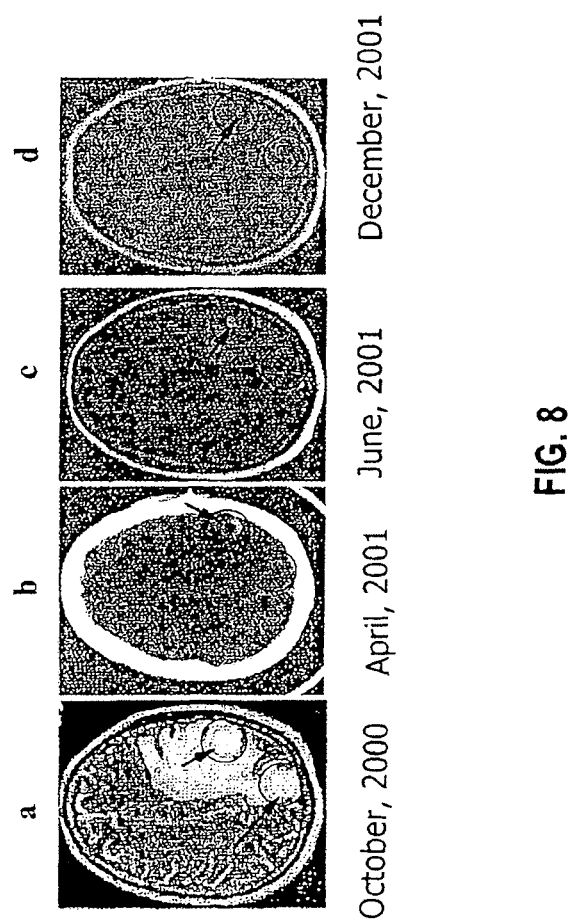

The antitumor efficacy of 2-hydroxyoleic acid and its analog oleic acid is shown in FIG. 8, in which we can see the disappearance of some cerebral tumor metastases, formed from a lung adenocarcinoma, after treatment with 2-hydroxyoleic acid. Treatment with this 2-hydroxyoleic acid and oleic acid caused complete disappearance of the cancer. These results demonstrate that (a) 2-hydroxyoleic acid and its analogs are molecules that can be used for making drugs intended for treating cancer; (b) that they have a broad spectrum of action (they have been effective on various types of tumor cells in culture and in living organisms) and (c) that they are superior to other molecules used for the treatment of cancer in their antitumor potency, in their absence of side effects and in that they are administered orally, although intravenous or subcutaneous administration is also possible.

—Antitumor Tests—

Figure 3:
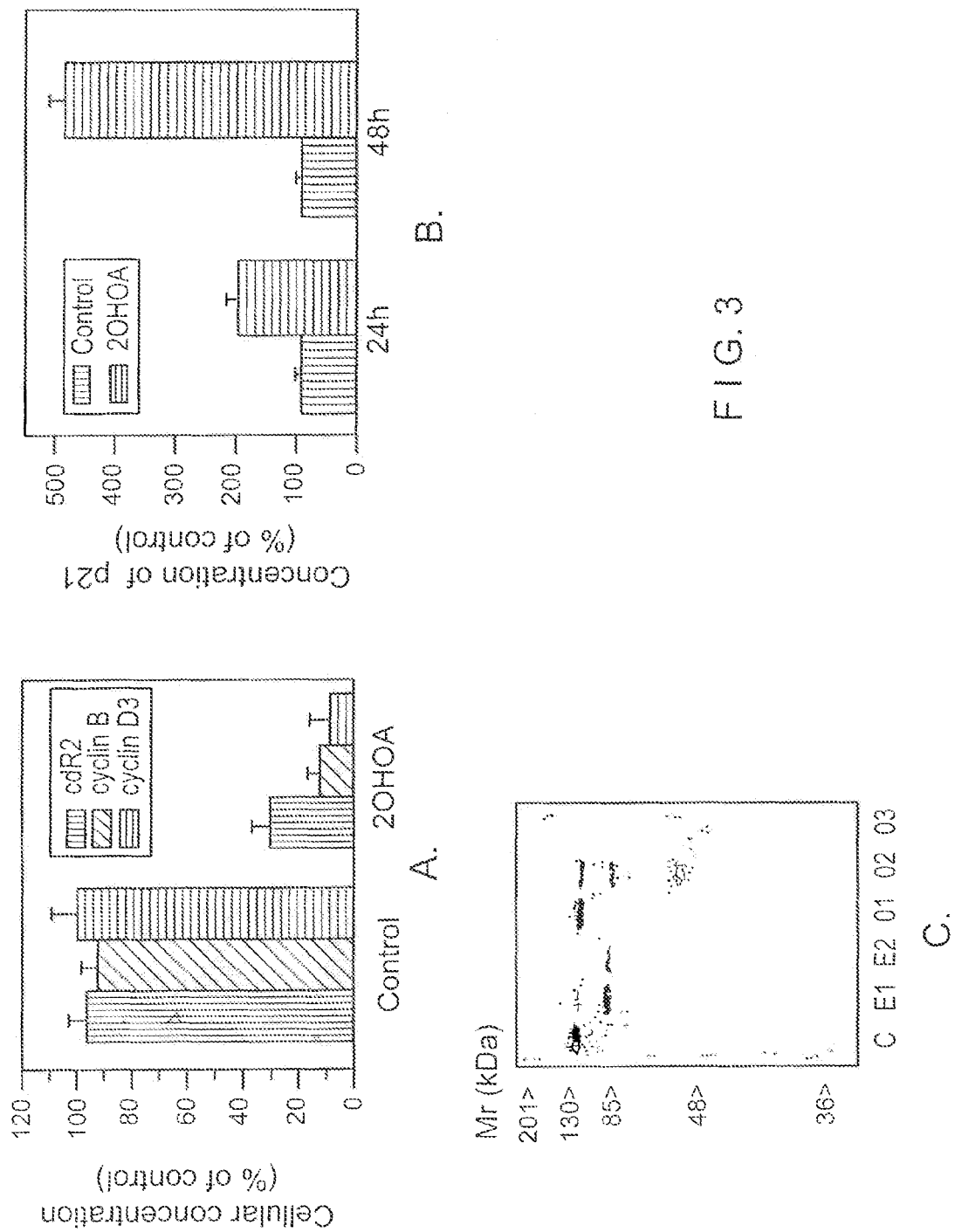

The antiproliferative efficacy of hydroxyoleic acid has been demonstrated in human lung cancer cells A549 and in human leukemia cells (Jurkat). FIG. 3 shows the induction of the antiproliferative protein p21, which is accompanied by a decrease in proteins cdk2, cyclin B and cyclin D3, necessary for the tumor cells to be able to divide. Similar effects were produced by all the analogs tested that comply with the general structural formula given earlier. This antiproliferative effect of 2-hydroxyoleic acid and its analogs was demonstrated by the reduction in cell density in tumor cells in culture (FIG. 4). This antiproliferative effect was also observed using other techniques and other cell types: in rat primary astrocytes, these fatty acids have an antiproliferative effect, which I studied by incorporating tritiated thymidine. Moreover, hydroxyoleic acid and its analogs are able to induce apoptosis or programmed cell death in human cancer cells. On the one hand, the degradation of PARP (FIG. 3C), and on the other hand the change in cellular morphology and the presence of cell residues (FIG. 4) demonstrate the effect of 2-hydroxyoleic acid and its analogs as inducers of cell death. Using flow cytometry experiments, it was established that in the presence of 2-hydroxyoleic acid the number of live human leukemia cells (Jurkat) was only 10% of those that remained alive with Etoposide, a known antitumor agent.

An objective of the present invention is to demonstrate that 2-hydroxyoleic acid and its analogs are agents with hypotensive activity.

Regulation of the Activity of G-Proteins Controls Blood Pressure.

Figure 7:
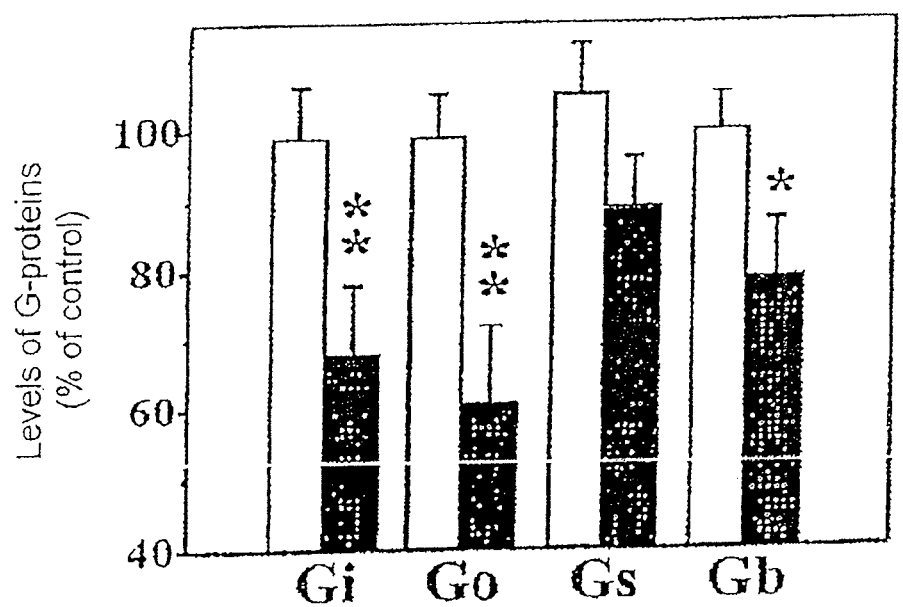

There is a relationship between the drugs of the invention and the activity of G-proteins and blood pressure. A result that confirms what was described earlier is a study carried out in humans, where it was seen that hypertensive individuals have changes in the levels of membrane lipids (Table 3). The membrane lipids have an influence on the lamellar-hexagonal transition, which in its turn determines the localization and functionality of G-proteins. In fact, in patients with hypertension, we observe a change in the levels of G-proteins bound to the membrane which is due to the aforementioned change in membrane lipids and the ease of forming hexagonal phases. If the modulation of non-lamellar membrane structures and the consequent relocalization of the G-proteins produces hypertension, by regulating the lamellar-hexagonal transition of the membrane lipids it is possible to achieve regulation of the localization of the membrane proteins and, finally, of blood pressure (FIG. 7).

TABLE 3

Composition of fatty acids of phospholipids and esters of cholesterol in erythrocyte membranes in normotensive (control) and hypertensive subjects (mg/100 mg).

| | Phospholipids | | Esters Patients | |
| --- | --- | --- | --- | --- |
| Fatty acid | Patients with hypertension | Controls | with hypertension | Cholesterol Controls |
| C14:0 | 0.4 ± 0.1 | 0.2 ± 0.1 | 0.9 ± 0.3 | 1.0 ± 0.2 |
| C14:1n-5 | 1.7 ± 0.2 | 2.2 ± 0.3** | 0.7 ± 0.2 | n.d.*** |
| C16:0 | 23.7 ± 0.6 | 23.1 ± 0.5 | 5.1 ± 0.6 | 14.3 ± 0.5* |
| C16:1n-9 | 0.4 ± 0.0 | 0.3 ± 0.0 | 3.1 ± 0.6 | 2.5 ± 0.3** |
| C16:1n-7 | 0.5 ± 0.0 | 0.5 ± 0.1 | 2.4 ± 0.4 | 1.7 ± 0.1*** |
| C16:4n-3 | 2.6 ± 0.3 | 2.5 ± 0.5 | n.d. | n.d. |
| C18:0 | 16.6 ± 0.3 | 17.1 ± 0.6 | 3.2 ± 0.5 | 2.9 ± 0.5 |
| C18:1n-9t | 0.9 ± 0.1 | 0.6 ± 0.0*** | n.d. | n.d. |
| C18:1n-9 | 16.3 ± 0.6 | 16.0 ± 0.8 | 18.4 ± 1.2 | 16.7 ± 0.6** |
| C18:1n-7 | 1.8 ± 0.1 | 2.0 ± 0.2** | 1.5 ± 0.1 | 1.7 ± 0.2** |
| C18:2n-6 | 12.5 ± 0.7 | 13.4 ± 0.7* | 45.8 ± 2.8 | 51.1 ± 1.6*** |
| C18:3n-6 | 0.4 ± 0.0 | n.d.*** | 0.9 ± 0.2 | 0.8 ± 0.1** |
| C18:3n-3 | 0.3 ± 0.0 | 0.4 ± 0.1 | n.d. | n.d. |
| C20:2n-6 | 2.1 ± 0.1 | 2.1 ± 0.2 | 0.9 ± 0.1 | 0.9 ± 0.1 |
| C20:4n-6 | 17.0 ± 0.4 | 16.5 ± 0.4 | 7.0 ± 0.6 | 6.4 ± 0.9* |
| C22:4n-6 | 0.7 ± 0.3 | 0.6 ± 0.1 | n.d. | n.d. |
| C22:6n-3 | 0.7 ± 0.1 | 0.8 ± 0.2 | n.d. | n.d. |
| C24:1n-9 | 1.5 ± 0.1 | 1.6 ± 0.1 | n.d. | n.d. |
| Total SFA | 41.2 ± 1.1 | 41.1 ± 0.7 | 19.3 ± 1.2 | 18.2 ± 1.1* |
| Total MUFA | 22.6 ± 0.6 | 21.7 ± 0.7* | 25.9 ± 1.6 | 22.7 ± 0.8*** |
| Total PUFA | 36.2 ± 1.2 | 38.2 ± 0.9** | 54.8 ± 2.4 | 59.1 ± 1.6*** |
| PUFA:SFA | 0.8 ± 0.04 | 0.9 ± 0.03 | 2.7 ± 0.3 | 3.4 ± 0.3*** |
| PUFA:MUFA | 1.6 ± 0.1 | 1.7 ± 0.1 | 2.2 ± 0.2 | 2.6 ± 0.2*** |

The values are mean values ± standard error of the mean (n = 28).
SFA, saturated fatty acids;
MUFA, monounsaturated fatty acids;
PUFA, polyunsaturated fatty acids.
*$P < 0.05$,
**$P < 0.01$,
***$P < 0.001$.
n.d.: not detected.

Finally, investigation of the effect in humans has revealed that 2-hydroxyoleic acid and its analogs may constitute a family of antitumor drugs of great importance. FIG. 8 shows the effect of treatment with 2-hydroxyoleic acid and oleic acid on tumors in humans. The case shown corresponds to a female patient in whom previous chemotherapy and radiotherapy did not produce reductions of brain tumors.

Figure 9:
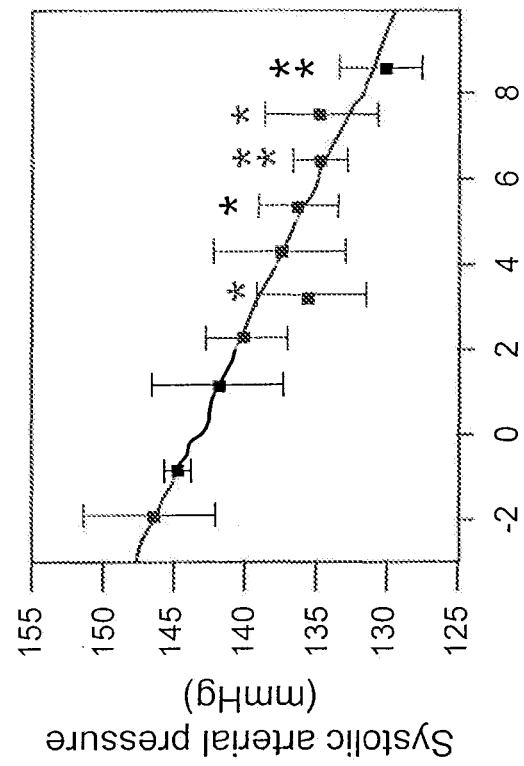
Figure 9:
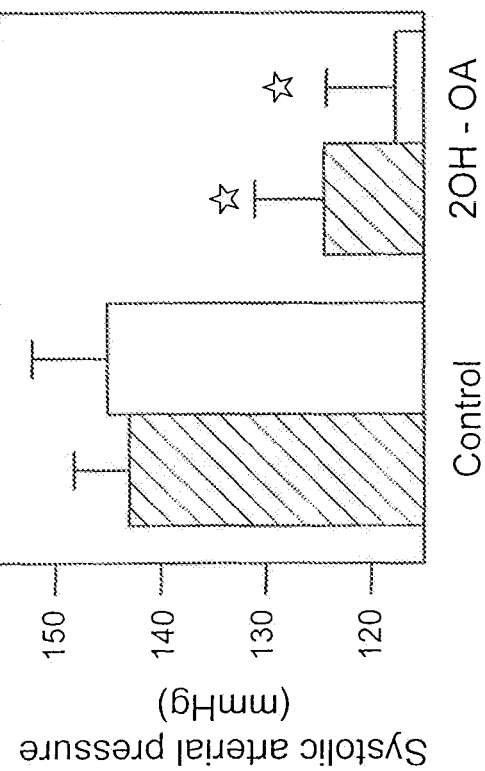
Figure 10:
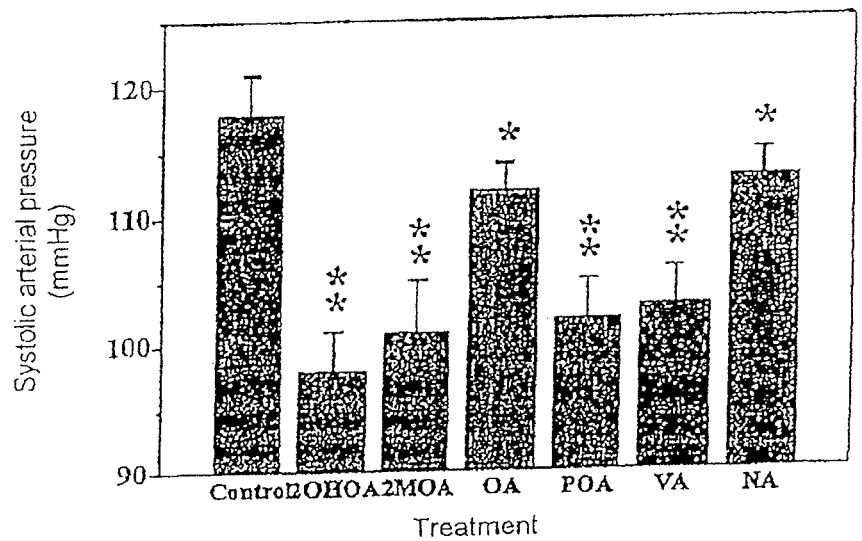

It was demonstrated that 2-hydroxyoleic acid and its analogs also have a marked hypotensive effect, since they induce reductions in systolic and diastolic blood pressure, without altering the heart rate (FIGS. 9a, 9b and 10). The hypotensive effect produced by 2-hydroxyoleic acid and its analogs is that it induces a reduction in blood pressure of an acute form (which is evident from 2 hours of treatment) and chronic (which is maintained for days and weeks while the treatment is maintained). Aminoleic acid, for example, reduces blood pressure by 15 mmHg in chronic treatments lasting a week.

Blood pressure is controlled by various systems of receptors coupled to G-proteins, such as vasopressin receptors, adrenergic receptors, etc.

Interaction between the hormones involved in the control of blood pressure with the receptors bound to stimulating G-proteins is modulated by the action of 2-hydroxyoleic acid and similar molecules.

These fatty acids regulate communication between receptor, G-protein and effector. The result is a modulation of the signals of cyclic AMP, phospholipase C and nitric oxide, which gives rise to a reduction in blood pressure. This effect is also connected with regulation of the membrane structure. The main pharmacological advantage of 2-hydroxyoleic acid and its analogs is that, in contrast to other hypotensive drugs, they do not have effects on the heart rate (i.e. they do not significantly increase or decrease the heart rate). An additional advantage of these compounds is that they control other cardiovascular risk factors: the serum lipid/lipoprotein profile and body weight (see below). Since control of blood pressure is not sufficient on its own to prolong a patient's life and that it is necessary to control other cardiovascular risk factors, these fatty acids are superior to other molecules employed in patients with cardiovascular diseases.

—Hypotensive Tests—

2-Hydroxyoleic acid induced significant reductions of blood pressure in rats (FIG. 9). These reductions were of an acute form (at 2 hours of treatment, 19±6 mmHg, P<0.01, n=6) and of a chronic form (1 week, 26±7 mmHg, P<0.001, n=6). Furthermore, acute and chronic treatments from 1 mg/kg to 10 mg/kg also produced significant reductions in blood pressure that were concentration-dependent.

In humans, 2-hydroxyoleic acid also produced significant, large decreases in blood pressure, see FIG. 9.

Moreover, the analogs of 2-hydroxyoleic acid that comply with the general formula given above had a hypotensive effect (FIG. 10). In all cases, the decreases in blood pressure were significant in comparison with the controls (*P<0.05, **P<0.01).

These results clearly show that 2-hydroxyoleic acid and its analogs are effective agents for clinical/pharmacological treatment of high blood pressure.

Figure 11:
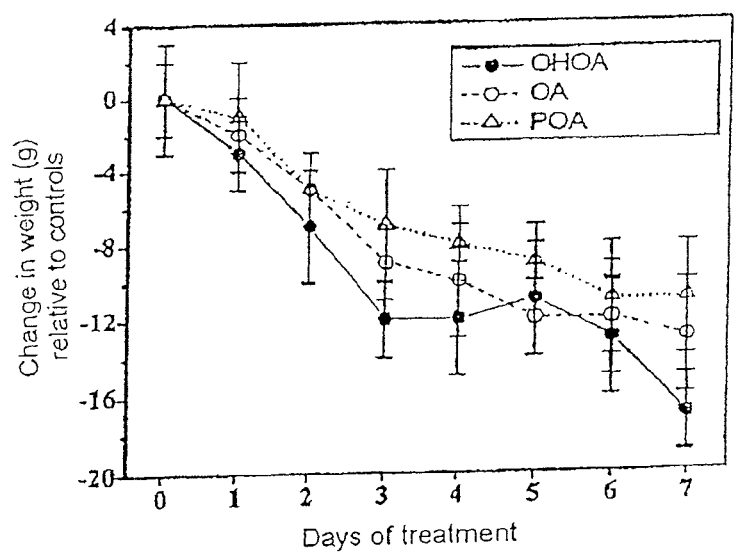

An objective of the present invention is to demonstrate that 2-hydroxyoleic acid and its analogs possess activity as agents that induce reductions in body weight (FIG. 11).

In addition to the antitumor and hypotensive activity of 2-hydroxyoleic acid and its analogs, they induce reductions in body weight.

Body weight is regulated by, among other things, factors such as the individual's metabolic capacity and control of food intake.

Control of food intake is determined by the feeling of satiety, which in turn is regulated at the hormonal level. For example, deficiency of nutrients stimulates the secretion of hormones which give rise to a sensation of appetite. After eating, once the nutrient levels have been restored, there is stimulation of the secretion of hormones that give rise to a feeling of satiety.

It has been found that 2-hydroxyoleic acid and its analogs produce effects of satiety, inducing reductions in food intake. This control is also mediated by receptors of cytokines, leptins, adrenoceptors, and other receptors coupled to G-proteins, whose activity is modulated by these fatty acids.

In the animals treated, this effect on satiety meant a consumption of feed between 15% and 30% less than the control animals.

—Tests of Control of Body Weight—

Rats treated with these molecules lost body weight during chronic treatments (from 5 to 17 days). In these experiments, rats treated with 2-hydroxyoleic acid or its analogs, in particular aminoleic acid, had free access to food and water, in the same way as the control group of treated rats (FIG. 11). In these conditions there was a progressive decrease in the rats' body weight starting from the first day of treatment, up to 17 grams on the seventh day of treatment (5% of the normal body weight of a Sprague-Dowley rat aged 2-3 months). The feed supplied to these animals was weighed and the consumption was found to be lower during the treatment time, confirming that the treatments with the molecules relating to this invention produce an effect of satiety in the animal. Similar experiments carried out on adult mice, for periods of up to 28 days with 2-hydroxyoleic acid, show reductions in body weight from 15% to 25%, relative to control mice (treated with vehicle).

DESCRIPTION OF THE DIAGRAMS

FIG. 1: Some of the many structures, in addition to lamellar, that the membranes can adopt.

FIG. 2 shows the cellular localization of $G\alpha i_2$ protein labeled with fluorescein in primary astrocytes of rat brain. In control cells, the labeling indicates the presence of this protein throughout the cell, especially in the nucleus (arrow). In cells treated with 2-hydroxyoleic (2OHOA), the labeling appears in membrane and cytosol, but not in the nucleus (arrow).

FIG. 3 shows the effect of 2-hydroxyoleic acid in molecular markers of cell proliferation and cell death. Part A shows the effect of 2-hydroxyoleic acid (2OHOA) on the cell cycle proteins cdk2, cyclin B and cyclin D3 in human lung cancer cells A549. The decrease in these proteins shows that this fatty acid induces stopping of the cell cycle, i.e. stopping of cell division. Part B shows the effect of 2-hydroxyoleic acid (2OHOA) on p21 protein in A549 cells after incubation for 24 and 48 hours. Protein p21 inhibits the cell cycle, so it is an antiproliferative protein. The large increases that 2-hydroxyoleic acid induces on this protein explain the stopping of the cycle and the proliferation of tumor cells. Part C shows the degradation of poly-ADP ribose polymerase (PARP) in human leukemia cells (Jurkat) (Etoposide: 25 [E1] and 250 µM [E2]; 2-hydroxyoleic acid: 10 [O1], 100 [O2] and 1000 µM [O3]). The decrease in levels of this enzyme, or evidence of its degradation, indicate the start of apoptosis or programmed cell death. In these experiments Etoposide was used as the positive control, as this molecule is known to be an inducer of apoptosis and an antitumor agent.

FIG. 4 shows the effect of 2-hydroxyoleic acid and its analogs on the proliferation of human lung cancer cells A549 (A) and Jurkat cells of human leukemia (B). Both 2-hydroxyoleic acid (2OHOA) and its analogs, all of which comply with the formula given previously, induce stoppage of division and the death of tumor cells (OA: oleic acid; VA: cis-vaccenic acid; POA: palmitoleic acid; NA: nervonic acid; 2MOA: 2-methyl oleic acid; 2NOA: 2-amino oleic acid.

FIG. 5 shows the binding of [$^{35}$S]GTPγS to membranes of NIH 3T3 cells transfected with the rat adrenoceptor $\alpha_{2A/D}$. This parameter measures the activity of G-proteins. The presence of 2-hydroxyoleic induces a decrease in function of the G-proteins even greater than the anthracycline daunomycin (DNM). The anthracyclines are potent antitumor drugs, therefore 2-hydroxyoleic is potentially more effective against tumors. The analogs of 2-hydroxyoleic produce an effect similar to that of 2-hydroxyoleic acid.

FIG. 6: Hydroxyoleic acid and its analogs had no effect on pure G-proteins (in the absence of membrane). This shows that its effect on the activity of G-proteins is mediated by the regulation of the non-lamellar membrane structures. Daunomycin (DNM) had a behavior similar to the control.

FIG. 7: Levels of G-proteins in membranes of erythrocytes of normotensive subjects (empty bars) and hypertensive subjects (filled bars). The levels of proteins $G\alpha i_{1/2}$ (Gi), $G\alpha o$ (Go), $G\alpha s$ (Gs) and G $G\beta$ (Gb) are significantly lower in hypertensive subjects. The values of the bars are mean values±standard error of the mean *$P<0.05$, **$P<0.01$.

FIG. 8 shows brain metastases (tumors) formed from a lung adenocarcinoma. The image on the left (8*a*) corresponds to the tumors before treatment and those on the right (8*b*, 8*c* and 8*d*) correspond to the tumors after treatment with 2-hydroxyoleic on various dates. As can be seen, one of the tumors disappeared more quickly and the other one more slowly.

FIG. 9*a* shows the acute effect (2 hours, black bars) and chronic effect (3 daily injections for 7 days, white bars) of hydroxyoleic acid (30 mg/kg) on the systolic arterial pressure in Sprague-Dowley rats. Lower doses of this molecule (1-10 mg/kg) produced similar effects, but less marked. *$P<0.01$.

FIG. 9*b* shows the effect of 2-hydroxyoleic acid (30 mg/kg) on blood pressure in humans. This diagram shows systolic arterial pressure as a function of the day of treatment. The days prior to treatment are shown with negative values. *$P<0.05$, **$P<0.01$.

FIG. 10 shows the effect of acute treatments with 2-hydroxyoleic acid (2OHOA) and its analogs 2-methyl oleic acid (2MOA), oleic acid (OA), palmitoleic acid (POA), cis-vaccenic acid (VA) and nervonic acid (NA). All the treatments carried out with 2-hydroxyoleic acid and the analogs that comply with the general formula given above induced significant decreases (*$P<0.05$, **$P<0.001$) in systolic arterial pressure in Sprague-Dowley rats.

FIG. 11 shows the effect of 2-hydroxyoleic acid (OHOA) and its analogs, oleic acid (OA) and palmitoleic acid (POA), on body weight (3 daily injections of 30 mg/kg). The animals (Sprague-Dowley rats) had free access to food and water at any time.

The invention claimed is:

1. A method for treating obesity comprising administration of an effective amount 2-hydroxyoleic acid or a pharmaceutically acceptable salt of 2-hydroxyoleic acid to a mammal in need thereof.

2. The method according to claim 1, comprising administering to the mammal the pharmaceutically acceptable salt of 2-hydroxyoleic acid.

3. The method according to claim 1, comprising administering to the mammal 2-hydroxyoleic acid.

\* \* \* \* \*